(12) United States Patent
Merkel et al.

(10) Patent No.: US 7,101,558 B2
(45) Date of Patent: Sep. 5, 2006

(54) HIGH YIELD PERTUSSIS VACCINE PRODUCTION STRAIN AND METHOD FOR MAKING SAME

(75) Inventors: Tod J. Merkel, Bethesda, MD (US); Jerry M. Keith, Olney, MD (US); Xiaoming Yang, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 127 days.

(21) Appl. No.: 10/312,272

(22) PCT Filed: Jun. 26, 2001

(86) PCT No.: PCT/US01/20356

§ 371 (c)(1),
(2), (4) Date: Dec. 20, 2002

(87) PCT Pub. No.: WO02/00895

PCT Pub. Date: Jan. 3, 2002

(65) Prior Publication Data

US 2006/0154354 A1    Jul. 13, 2006

Related U.S. Application Data

(60) Provisional application No. 60/214,072, filed on Jun. 26, 2000.

(51) Int. Cl.
*A61K 39/02* (2006.01)
*A01N 63/00* (2006.01)

(52) U.S. Cl. ............... 424/200.1; 424/93.4; 424/93.2; 424/234.1

(58) Field of Classification Search ............... 424/93.4, 424/93.1, 93.2, 200.1, 234.1; 435/69.3, 69.1
See application file for complete search history.

(56) References Cited

U.S. PATENT DOCUMENTS 5,643,747 A * 7/1997 Baker et al. ............... 435/69.1
5,705,361 A   1/1998 Walker et al. ............. 435/69.3

FOREIGN PATENT DOCUMENTS

EP            0396964      * 10/1989

OTHER PUBLICATIONS

Walker et al. Infect. Immun. 59: 4238-4248, 1991.*
Lee et al. Infect. Immun. 57: 1413-1418, 1989.*
Martinez et al. Mol. Microbiol. 22: 895-908, 1996.*
Giardina et al. J. Bacteriol. 177: 6058-6063, 1995.*
Burnette et al. Pertussis toxin S1 mutant with reduced enzyme activity and a conserved protective epitope. *Science*. 242:72-74. (1988).
Cieplak et al. Identification of a region in the S1 subunit of pertussis toxin that is required for enzymatic activity and that contributes to the formation of a neutralizing antigenic determinant. *Proceedings of the National Academy of Sciences of the U.S.A.* 85:4667-4671 (1988).
Cotter et al. Filamentous hemagglutinin of *Bordetella bronchiseptica* is required for efficient establishment of tracheal colonization. *Infect. Immun.* 66(12):5921-5929. (1998).
Lobet et al. Site-specific alterations in the B oligomer that affect receptor-binding activities and mitogenicity of pertussis toxin. *Journal of Experimental Medicine*. 177:79-87. (1993).
Pizza et al. Mutants of pertussis toxin suitable for vaccine development. *Science*. 246:497-500. (1989).
Suarez et al. Stable expression of pertussis toxin in *Bordetella bronchiseptica* under the control of a tightly regulated promoter. *Applied and Environmental Microbiology*. 63(1):122-127. (1997).

* cited by examiner

*Primary Examiner*—S. Devi
(74) *Attorney, Agent, or Firm*—Needle & Rosenberg, P.C.

(57) ABSTRACT

The present invention provides a vaccine production strain of *Bordetella bronchiseptica* that produces a pertussis toxin in high yield. The present invention provides a method for creating a *Bordetella bronchiseptica* cell line which produces a *Bordetella pertussis* toxin comprising the steps of introducing a plasmid containing a DNA encoding antibiotic resistance into a *Bordetella bronchiseptica* strain, selecting for isolates in which the DNA encoding antibiotic resistance is recombinantly incorporated into the chromosome in place of the *Bordetella bronchiseptica* toxin gene, introducing a plasmid containing DNA encoding subunits of the *Bordetella pertussis* toxins into the *Bordetella bronchiseptica* isolates; and, selecting for isolates in which DNA encoding *Bordetella pertussis* toxin subunit is recombinantly incorporated into the chromosome, the resulting cells producing the *Bordetella pertussis* toxin. The present invention further provides a method for creating a *Bordetella bronchiseptica* cell line which produces a *Bordetella pertussis* toxin and does not express filamentous hemagglutinin.

2 Claims, 12 Drawing Sheets

Immunoblot Analysis of Pertussis Toxin with Monoclonal Antibody 1B7

| MgSO₄ | PT | GP1SN | TY168 | TY178 | FHA |
|---|---|---|---|---|---|
| Supernatant | + | - | + | - | - |
| Cells | + | - | + | - | - |

PT: purified pertussis toxin.
FHA: purified filamentous hemagglutinin.

FIG. 7A

HIGH YIELD PERTUSSIS VACCINE PRODUCTION STRAIN AND METHOD FOR MAKING SAME

The present application is a 35 U.S.C. § 371 national phase application from, and claims priority to, international application PCT/US01/20356, filed Jun. 26, 2001 published under PCT Article 21(2) in English), which claims priority to U.S. Provisional application No. 60/214,072, filed Jun. 26, 2000, which applications are incorporated herein in their entirety by this reference.

BACKGROUND OF THE INVENTION

Whooping cough, or pertussis, is a severe infectious human respiratory tract disease brought about by *Bordatella pertussis*. The disease typically manifests itself in children and immunization is accomplished by initial vaccination of children in their infancy followed by repeated vaccination during the early years of their childhood.

Historically, pertussis vaccines in the art were prepared using whole-cell heat-killed bacteria. The use of these vaccines, however, had a number of drawbacks in administration and in the adverse side effects that resulted from their administration. Over time, health care administrators attributed a decrease in the administration rate of pertussis vaccines and a corresponding increase in the incidence of whooping cough in children to these drawbacks.

More recently, researchers have developed acellular vaccines which have been proven to have milder side effects. The central component of these recently developed vaccine strains is the pertussis toxin. According to methods now known in the art, prior to use, the pertussis toxin is detoxified by either chemical detoxification or by recombinant production of genetically detoxified toxin containing mutations for several different variations that produce the detoxified toxin. See, e.g., U.S. Pat. No. 5,785,971, issued to R. Rappuoli, et al., U.S. Pat. No. 5,733,600 issued to W. N. Burnette; and, EPO Publication No. EP 0 396 964 B1, in the name of Pizza, et al.

While the administration drawbacks of pertussis vaccines of the past have been overcome by the development and introduction of acellular vaccines, problems associated with producing sufficient quantities of these vaccines remain. The pertussis toxin is a complex multi-component antigen that is made up of five sub-units, S1–S5. The difficulties in large quantity production of the toxin are several. The bacterium conventionally used to produce the toxin is difficult to grow and grows slowly. It does not reliably produce the toxin in large quantities when grown in culture. Moreover, the toxin produced by the bacterium is difficult to purify from its most significant contaminant, filamentous hemagglutinin. Thus, presently, there is no vaccine production strain that produces assembled pertussis toxin with high yield and purity and which grows rapidly and reliably. Nor is there one that produces such a pertussis toxin that is substantially, if not totally, free of filamentous hemagglutinin.

SUMMARY OF THE INVENTION

The present invention overcomes the shortcomings of acellular pertussis vaccine production strains in the art by providing a genetically modified strain of *Bordatella bronchiseptica* that produces a pertussis toxin.

The present invention overcomes the shortcomings of *Bordatella pertussis* vaccine production strains in the art by providing a pertussis toxin production strain which grows at a higher rate, in a less expensive medium, and more reliably than currently available *Bordatella pertussis* vaccine production strains.

The present invention provides a novel genetically modified strain of *Bordatella bronchiseptica* that produces a pertussis toxin which reduces production costs and increases facility capacity.

Moreover, the present invention overcomes the shortcomings of pertussis vaccine production strains in the art by providing a method for producing a pertussis toxin which is purer than pertussis toxins produced by methods heretofore known in the art.

The present invention provides a *Bordetella bronchiseptica* strain wherein the entire region of the *Bordetella bronchiseptica* toxin gene is replaced by DNA that expresses subunits S1 through S5 of the *Bordetella pertussis* toxin.

The present invention provides a first novel plasmid having the structure of pTM180 as shown in FIG. 1A.

The present invention provides a second novel plasmid having the structure of pTM181 as shown in FIG. 1B.

The present invention provides a third novel plasmid having the structure of pTY008 as shown in FIG. 6.

The present invention provides a method for creating a *Bordetella bronchiseptica* cell line which produces a *Bordetella pertussis* toxin. The method includes at least the steps of introducing a plasmid containing a DNA encoding antibiotic resistance into a *Bordetella bronchiseptica* strain, selecting for isolates in which the DNA encoding antibiotic resistance is recombinantly incorporated into the chromosome in place of the *Bordetella bronchiseptica* toxin gene, introducing a plasmid containing DNA encoding subunits S1 through S5 of the *Bordetella pertussis* toxin into the *Bordetella bronchiseptica* isolates in place of the DNA encoding antibiotic resistance; and, selecting for isolates in which DNA encoding *Bordetella pertussis* toxin subunits S1 through S5 is recombinantly incorporated into the chromosome such that the resulting cells produce *Bordetella pertussis* toxin.

The present invention also provides a method for creating a *Bordetella bronchiseptica* cell line which produces a *Bordetella pertussis* toxin and does not express filamentous hemagglutinin. In this method, a DNA encoding antibiotic resistance is introduced into the *Bordetella bronchiseptica* strain produced by the above steps and isolates are selected in which the DNA encoding antibiotic resistance is recombinantly incorporated into the chromosome in a manner that disrupts the *Bordetella bronchiseptica* filamentous hemagglutinin gene. The resulting *Bordetella bronchiseptica* strain expresses pertussis toxin, but not filamentous hemagglutinin.

BRIEF DESCRIPTION OF THE DRAWINGS

FIG. 7A is an immunoblot analysis of pertussin toxin with monoclonal antibody 1B7.

DETAILED DESCRIPTION OF THE INVENTION

The present invention is more particularly described in the following examples which are intended as illustrative only since numerous modifications and variations therein will be apparent to those skilled in the art.

As used in the specification and in the claims, "a" can mean one or more, depending upon the context in which it is used.

The present invention provides a *Bordetella bronchiseptica* strain wherein the DNA encoding *Bordetella bronchiseptica* toxin is replaced by DNA encoding subunits S1 through S5 of the *Bordetella pertussis* toxin. *Bordatella bronchiseptica* is preferred for expressing pertussis toxin as it is capable of more rapid growth than *Bordetella pertussis*, and grows easily on more types of media than *Bordetella pertussis*.

In a first embodiment of this invention, a *Bordetella bronchiseptica* strain with the *Bordetella bronchiseptica* toxin gene deleted is used to generate a strain of *Bordetella bronchiseptica* that expresses the *Bordetella pertussis* toxin. An example of the toxin-deleted strain is exemplified by strain TY166. It is made by modification of a *Bordetella bronchiseptica* strain, for example GP1SN or BB55, in the steps described below. Moreover, in this embodiment, the *Bordetella bronchiseptica* strain resulting from replacement of the *Bordetella bronchiseptica* toxin DNA with DNA encoding subunits S1 through S5 of the *Bordetella pertussis* toxin is exemplified by strain TY168.

In a second embodiment, a *Bordetella bronchiseptica* strain is produced by replacement of the DNA encoding *Bordetella bronchiseptica* toxin with DNA encoding subunits S1 through S5 of the *Bordetella pertussis* toxin, and some or all of the DNA encoding filamentous hemagglutinin is deleted. The deletion can be complete or it can be a deletion of enough of the coding region to render the gene inactive or non-functional. In this embodiment, the resulting *Bordetella bronchiseptica* strain is exemplified by strain TY178.

Figure 1A:
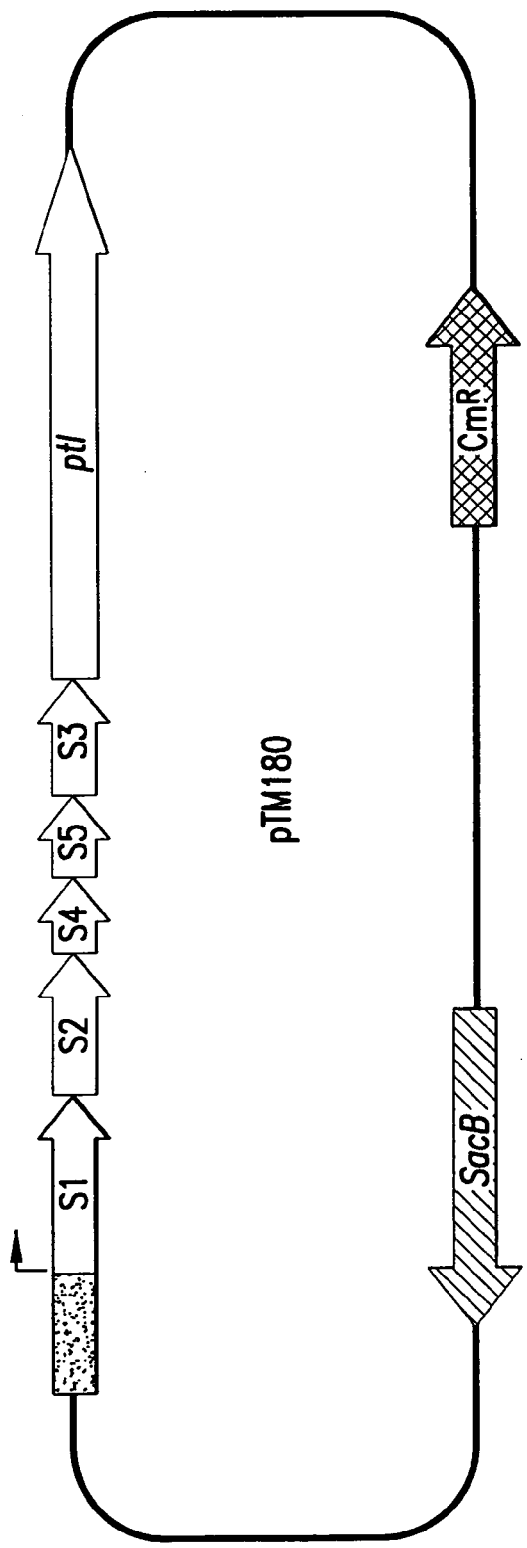
FIG. 1A illustrates the structure of plasmid pTM180. Shown in the figure are the sequence upstream of the pertussis toxin gene from *Bordetella pertussis*, the pertussis toxin genes and the liberation genes, which encode the products required for pertussis toxin secretion and assembly, and the genes conferring resistance to chloramphenicol ($Cm^R$) and sensitivity to high sucrose concentrations (sacB).

The present invention provides a novel plasmid having the structure of pTM180 as shown in FIG. 1A. The plasmid is a suicide plasmid containing DNA encoding subunits S1 through S5 of the *Bordetella pertussis* toxin along with the regulatory sequences required for expression of the toxin, i.e., the *Bordetella pertussis* DNA sequences upstream and downstream of the ptx region.

Figure 1B:
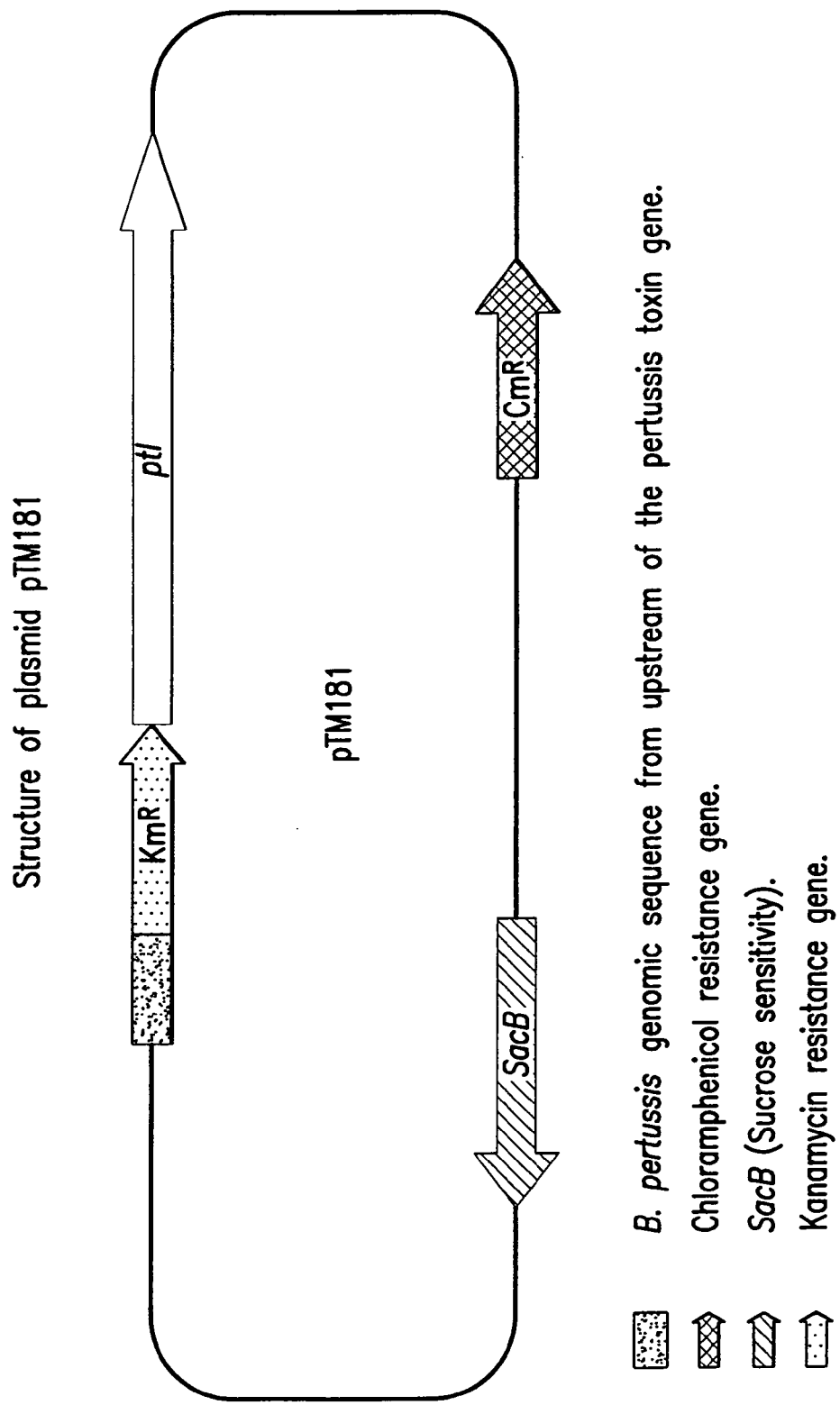
FIG. 1B shows the structure of plasmid pTM181. Shown in the figure are the pertussis liberation genes and the genes conferring resistance to chloramphenicol ($Cm^R$) and kanamycin ($Km^R$), and sensitivity to high sucrose concentrations (sacB).

The present invention also provides a novel plasmid having the structure of pTM181 as shown in FIG. 1B. The plasmid is a suicide plasmid containing DNA encoding kanamycin resistance inserted in place of the region encoding the pertussis toxin S1–S5 subunits.

Figure 6:
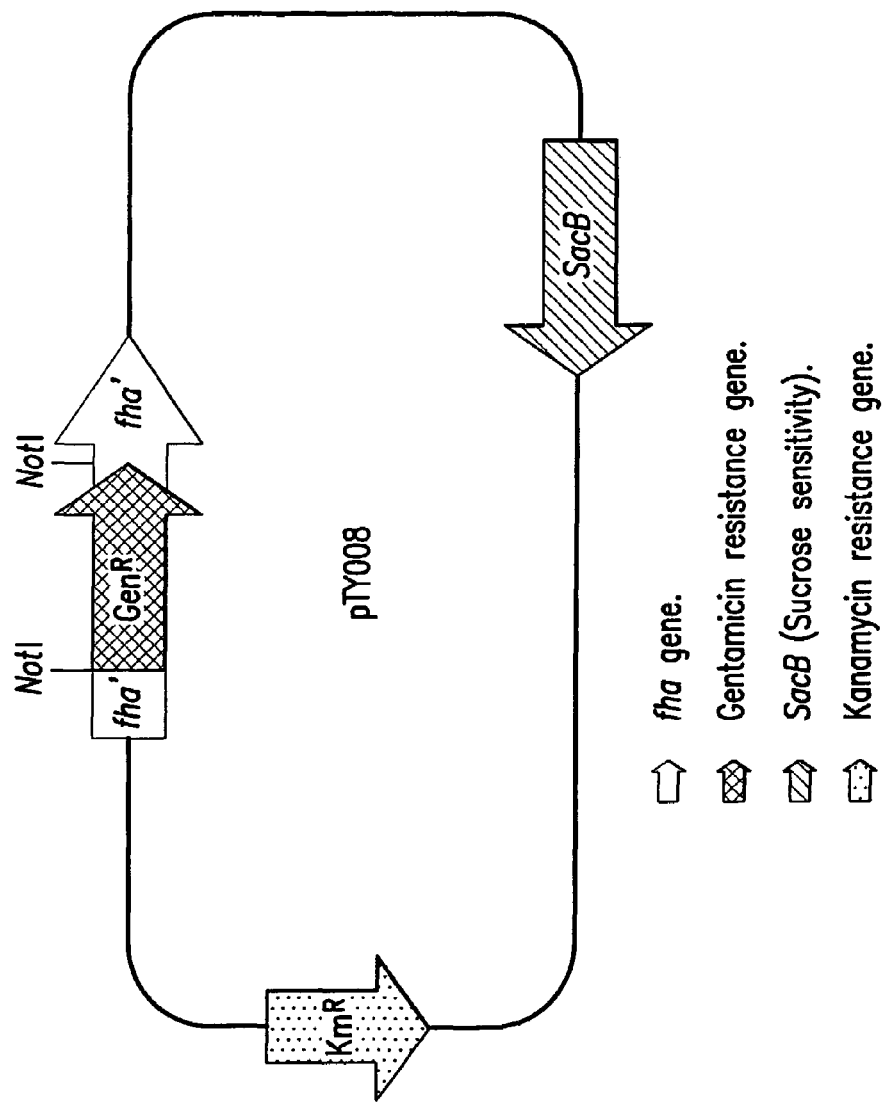
FIG. 6 illustrates the structure of plasmid pTY008. Shown in the figure are the filamentous hemagglutinin gene (fha), as well as the genes conferring resistance to kanamycin ($Km^R$) and gentamicin ($Gm^R$) and sensitivity to high sucrose concentrations (sacB).

The present invention further provides a novel plasmid having the structure of pTY008 as shown in FIG. 6. The plasmid is a suicide plasmid containing DNA encoding gentamicin resistance inserted in place of the internal NotI fragment of the filamentous hemagglutinin gene.

The present invention provides a method for creating a *Bordetella bronchiseptica* cell line which produces a *Bordetella pertussis* toxin upon the completion of a series of single cross-over events that result in the replacement of the *Bordetella bronchiseptica* toxin genes with the *Bordetella pertussis* toxin genes.

In summary, the method comprises three steps:

1) the replacement of the *Bordetella bronchiseptica* toxin genes with the gene encoding kanamycin resistance to generate a strain exemplified by strain TY166;

2) the subsequent replacement of the gene encoding kanamycin resistance in strain TY166 with the genes (S1–S5) encoding the *Bordetella pertussis* toxin genes to generate a strain exemplified by strain TY168; and 3) the replacement of at least a portion of the fhaB gene coding region with the gene encoding gentamicin resistance. In this final step it is preferred that the internal ¾ths of the fhaB gene coding region is replaced with the gene encoding antibody resistance. As illustrated in the examples, the antibody resistance described herein is gentamicin resistance.

More particularly, the first method includes a step of introducing a plasmid containing a DNA encoding antibiotic resistance into a *Bordetella bronchiseptica* strain and selecting for isolates in which the DNA encoding antibiotic resistance is recombinantly incorporated into the chromosome in place of the *Bordetella bronchiseptica* toxin gene in a first recombination event, and a second step of introducing a plasmid containing DNA encoding subunits S1 through S5 of the *Bordetella pertussis* toxin into the antibiotic resistant *Bordetella bronchiseptica* isolates, in place of the DNA encoding antibiotic resistance, and selecting for isolates in which DNA encoding *Bordetella pertussis* toxin subunits S1 through S5 is recombinantly incorporated into the chromosome such that the resulting cells produce *Bordetella pertussis* toxin.

Those skilled in the art will recognize that other vehicles are available for incorporating DNA into the *Bordetella bronchiseptica* strain of the present invention. However, a suicide plasmid, is used in the methods of the present invention as it does not replicate inside bacterial cells and, therefore, does not get passed on to progeny bacterial cell unless they recombine into the bacterial chromosome. Suicide plasmids are engineered and have no sequences in them that are homologous to the chromosome such that they are able to homologously recombine with the chromosome due only to the homology between the exogenous DNA insert placed in the plasmid and the chromosomal DNA.

Bacteriocins are compounds produced by bacteria that inhibit growth of, or kill closely related species. Colicins are bacteriocins produced by some strains of *Escherichia coli* that kill *E. coli* as well as the closely related genera, Salmonella and Shigella. Because colicins kill only *E. coli*, Salmonella and Shigella, they are powerful counterselective agents in matings between *E. coli* strains and other gram negative bacteria. The present invention takes advantage of this fact to avoid the need for using *Bordetella bronchiseptica* strains marked with antibiotic resistance.

In the present invention, plasmids are transferred into *Bordetella bronchiseptica* by performing matings with the *E. coli* strain bearing the plasmid and the appropriate strain of *Bordetella bronchiseptica*. In this process, the mating mixture is plated on plates containing high levels of colicin and the antibiotic that corresponds to the antibiotic resistance encoded on the plasmid. Only *Bordetella bronchiseptica* cells that take up and maintain the plasmid survive. The *E. coli* donor is killed by the colicin. The *Bordetella bronchiseptica* recipient that fails to take up or maintain the plasmid is killed by the antibiotic.

The methods of the present invention can employ any *Bordetella bronchiseptica* strain, for example strain GP1 SN, as the base strain from which *Bordetella pertussis* toxin is ultimately derived. More particularly, in the first step, suicide plasmid pTM181 (FIG. 1B) is used to introduce antibiotic resistance into the *Bordetella bronchiseptica* strain GP1SN. According to the methods of this invention, the antibiotic resistance encoding genes contained within suicide plasmid pTM181 are incorporated into the bacterial chromosome by homologous recombination at a point within the region 1500 bp downstream or within the region 3000 bp upstream of the *Bordetella bronchiseptica* toxin genes on the chromosome and the homologous regions on the plasmid. This first crossover event results in the incorporation of the plasmid into the *Bordetella bronchiseptica* chromosome. The DNA encoding antibiotic resistance introduced by the pTM181 plasmid encodes kanamycin resistance and chloramphenicol resistance.

Next, isolates in which the plasmid sequences have been removed by an intragenic recombination event such that the DNA encoding antibiotic is retained in the chromosome in place of the *Bordetella bronchiseptica* toxin genes are then selected using kanamycin. The isolates are identified by selection for loss of the plasmid on plates containing high concentrations of sucrose with subsequent screening for the loss of chloramphenicol resistance. The success of the second crossover event is verified by assessing the pattern of colony death on antibiotic plates.

In the method of the present invention, the cleavage of sucrose by sucrase results in a metabolic intermediate that is toxic to many strains of bacteria when present in high concentrations. When such a bacterial strain harbors a plasmid that carries the gene encoding sucrase (the sacB gene), it is sensitive to high concentrations of sucrose. Where the strain is plated on high concentrations of sucrose, the sucrase enzyme cleaves the sucrose, the toxic metabolic intermediate accumulates and the cell dies. If the bacterial strain loses the plasmid, it becomes resistant to high concentrations of sucrose because it no longer expresses the sucrase enzyme.

The suicide plasmid bearing antibiotic resistance, the sacB gene and a region of homology to the chromosome is introduced into bacterial cells as described above and the cells are plated on the antibiotic. Only those bacterial cells in which the plasmid has crossed onto the chromosome by homologous recombination will form colonies on the antibiotic plate. The antibiotic resistant strain is plated on high concentrations of sucrose in absence of antibiotic. At a low frequency the plasmid will cross out spontaneously, therefore in the population of cells there will always be some that have lost the plasmid. Those few cells that have spontaneously lost the plasmid will not be expressing sucrase, therefore they will be able to grow in the presence of high concentrations of sucrose. The sucrose-resistant colonies are then checked by replica-plating on two plates; one with and one without the antibiotic. If the plasmid has been crossed out, the strain will be sensitive to the antibiotic and will not grow. This test is necessary because a mutation of the sacB gene on the plasmid will also render a strain resistant to high concentrations of sucrose even if the plasmid is still there. Therefore, only sucrose-resistant, antibiotic sensitive colonies can be safely considered to be plasmid free.

The resulting *Bordetella bronchiseptica* isolates are exemplified by strain TY166, a *Bordatella bronchiseptica* strain which lacks the *Bordatella bronchiseptica* toxin gene. This strain has been deposited in the ATCC Patent Depositary (American Type Culture Collection, 10801 University Blvd., Manassas, Va. 20110-2209) as PTA-2110, on Jun. 19, 2000.

As discussed herein, types of antibiotic resistance that are effective for use with the *Bordetella* strains of the present invention include gentamicin, chloramphenicol, kanamycin and mercury. Still other types of selection, such as colicin, for example, will be known to those skilled in the art. In the methods of the present invention, gentamicin, chloramphenicol and kanamycin are used at various stages to provide antibiotic resistance. While the methods of the present invention are described using these different types of antibiotic resistance at different stages, it will be apparent to those skilled in the art that these methods can also be accomplished using any one of the known or later identified types of antibiotic resistance, individually or in combination, provided that the same type of antibiotic resistance is not employed simultaneously in accomplishing the methods described in this invention.

The method of the present invention includes a second step in which plasmid pTM180 (FIG. 1A) is used to introduce DNA encoding subunits S1 through S5 of the *Bordetella pertussis* toxin into the *Bordetella bronchiseptica* strain TY166. In this step, the pTM180 plasmid crosses over somewhere in the region 1500 bp downstream or somewhere in the region 3000 bp upstream of the ptx genes on the plasmid and the homologous regions on the chromosome. Isolates in which the plasmid has been incorporated into the bacterial chromosome by homologous recombination between the *Bordetella pertussis* DNA insert on the plasmid and the homologous chromosomal DNA are then identified by selection on chloramphenicol plates. Subsequently, selection for sucrose resistant isolates and screening for kanamycin sensitive isolates was carried out. These isolates are the result of a second single intragene crossover event between the plasmid-encoded sequences and the chromosomal sequences in the region upstream or downstream of the *Bordetella pertussis* toxin genes on the plasmid and upstream or downstream of the kanamycin resistance gene on the chromosome of strain TY166 that results in the loss of the plasmid sequences and the replacement of the kanamycin resistant gene with the genes encoding the *Bordetella pertussis* toxin genes. The *Bordetella bronchiseptica* isolates selected by these steps are exemplified by strain TY168. This strain has been deposited in the ATCC Patent Depository (American Type Culture Collection, 10801 University Blvd., Manassas, Va. 20110-2209) as PTA-2109, on Jun. 19, 2000.

The present invention also provides a third step for creating a *Bordetella bronchiseptica* cell line which expresses a *Bordetella pertussis* toxin and does not express filamentous hemagglutinin. In this method, the third step is used to introduce a DNA encoding antibiotic resistance into the *Bordetella bronchiseptica* strain produced by the above steps (e.g., TY168). Isolates in which the DNA encoding antibiotic resistance are recombinantly incorporated into the chromosome in place of the *Bordetella bronchiseptica* filamentous hemagglutinin are selected.

More specifically, in the third recombination step, suicide plasmid pTY008 is employed to introduce a gene encoding gentamicin resistance into *Bordatella bronchiseptica* strain TY168 in at least a portion of the filamentous hemagglutinin gene. The isolates are the result of a single crossover event between the plasmid sequences and the chromosomal sequences at either the 5' end or the 3' end of the fhaB gene.

Subsequently, selection for sucrose and screening for gentamicin resistant conjugates from the above step was carried out. Such an isolate is the result of a single intragenic crossover event between the plasmid-encoded sequences and the chromosomal sequences at either the 5' end or the 3' end of the fhaB gene that results in the loss of the plasmid sequences and the replacement of the fhaB coding sequence with the gentamicin resistance gene. The *Bordetella bronchiseptica* isolates selected by these steps are exemplified by strain TY178. This strain has been deposited in the ATCC Patent Depository (American Type Culture Collection, 10801 University Blvd., Manassas, Va. 20110-2209) as PTA-2111, on Jun. 19, 2000.

As this crossover event takes place on a different part of the bacterial chromosome, it does not interfere with the methods and products described above. The *Bordatella bronchiseptica* strain resulting from this crossover includes no more than one-third of the filamentous hemagglutinin originally contained on the chromosome. The efficacy of this crossover step is verified as set forth below. The *Bordetella bronchiseptica* isolates selected by these steps are exemplified by strain BBPT, a *Bordetella bronchiseptica* capable of expressing and secreting a detoxified, high yielding pertussis toxin.

As those skilled in the art will recognize, other methods for knocking out the fhaB gene include but are not limited to deletion, insertion and point mutations that render the gene non-translatable or produce a version of the protein wherein the gene is at least partially deleted. While it is not necessary to cross-out the entire plasmid sequence when introducing the toxin genes or when knocking out the fhaB gene, in the preferred embodiment, the plasmid sequence is removed to provide recombinant bacterial strains that are more stable.

According to the present invention, detoxification of the pertussis toxin is achieved through amino acid substitution of at least at least one amino acid in the S1 subunit. Detoxification is also achievable wherein interaction of the toxin with targets cells is prevented through amino acid substitution of at least at least one amino acid in the S3 subunit. Where amino acid substitution on the S1 subunit yields the detoxified pertussis toxin, substitution occurs at position 9, or may occur at positions 9 and 129, as is preferred. The present strain of pertussis toxin is also useful for the production of wild type toxin or any of a variety of genetically modified versions of pertussis toxin. Such changes may include genetic changes within the pertussis toxin coding sequence (e.g. R9K or E129A in the pertussis toxin S1 subunit) or within the pertussis toxin regulatory regions. Still other methods for making genetic changes to the pertussis toxin to produce other modified versions of the toxin are disclosed in the References cited and discussed therein.

The following examples are provided to illustrate certain preferred embodiments of the invention, and do not suggest that the invention should be limited to what they describe. Other embodiments are within the routine reach of the skilled artisan given the teaching provided herein.

EXAMPLES

Figure 2:
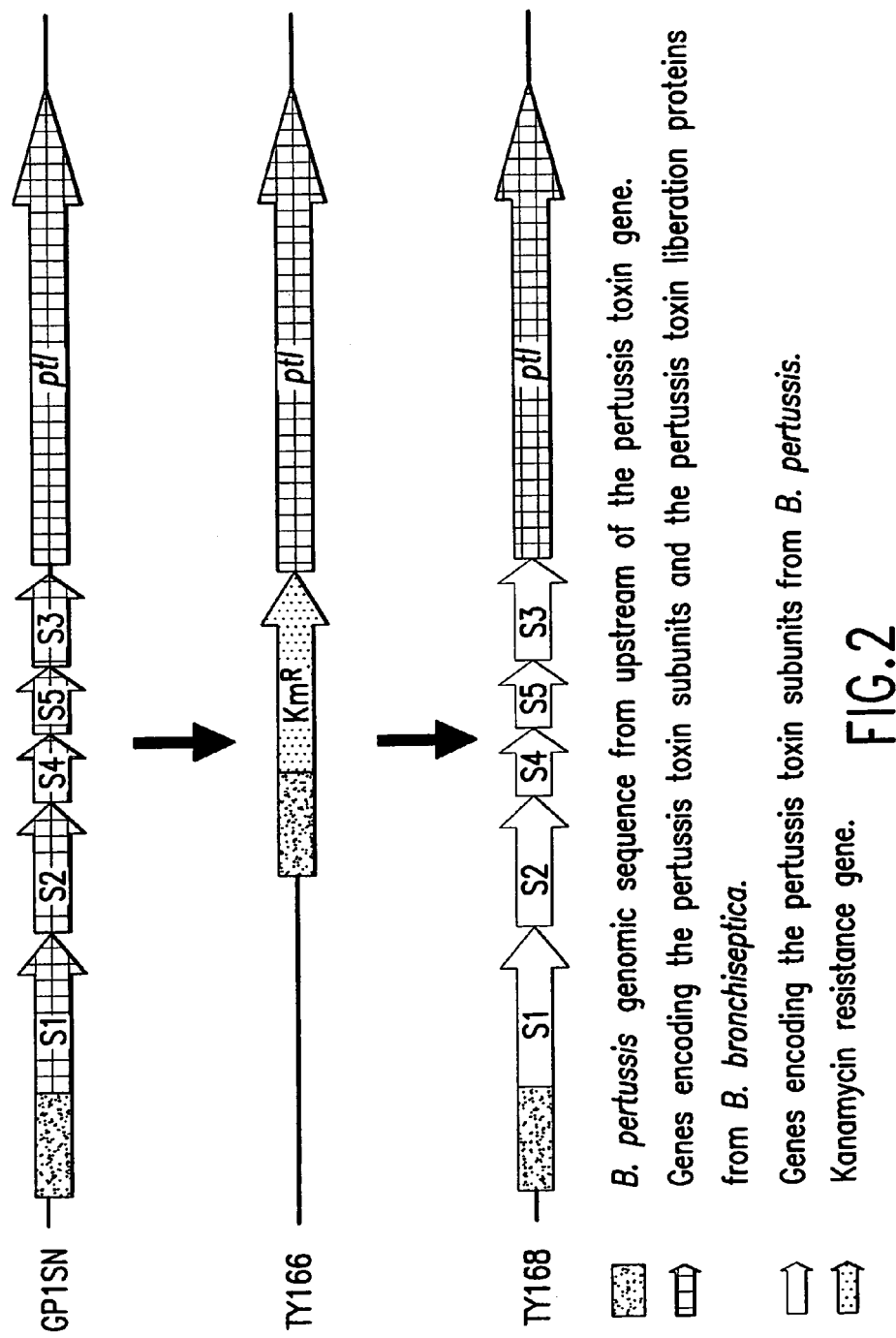
FIG. 2 illustrates the replacement of the pertussis toxin gene of *Bordetella bronchiseptica* with the pertussis toxin gene of *Bordetella pertussis* to produce *Bordetella bronchiseptica* Strain TY168.

The genes encoding the *B. bronchiseptica* toxin in *Bordatella bronchiseptica* strain GP1SN were replaced with the gene encoding kanamycin resistance in a two step process (FIG. 2). First suicide plasmid pTM181 (FIG. 1B) was introduced into strain GP1SN. Isolates in which the plasmid had been incorporated into the bacterial chromosome by homologous recombination between the *Bordatella* DNA insert on the plasmid and the homologous chromosomal regions were identified by selection on colicin-kanamycin plates. In the second step, rare isolates in which the plasmid sequences were crossed out by an intragenic recombination to yield strain TY 166 were identified by selecting for loss of the plasmid on plates containing kanamycin and high concentrations of sucrose with subsequent screening for the loss of chloramphenicol resistance.

The *Bordatella pertussis* genes encoding the S1 through S5 subunits of pertussis toxin were transferred onto the *Bordatella bronchiseptica* through a similar two-step process. First suicide plasmid pTM180 (FIG. 1A) was introduced into strain TY166. Isolates in which the plasmid had been incorporated into the bacterial chromosome by homologous recombination between the *Bordatella* DNA insert on the plasmid and the homologous chromosomal region were identified by selection on colicin-chloramphenicol plates. In the second step, rare isolates in which the plasmid sequences were crossed out by an intragenic recombination to yield strain TY168 were identified by selecting for loss of the plasmid on plates containing high concentrations of sucrose with subsequent screening for the loss of chloramphenicol and kanamycin resistance.

Figure 3:
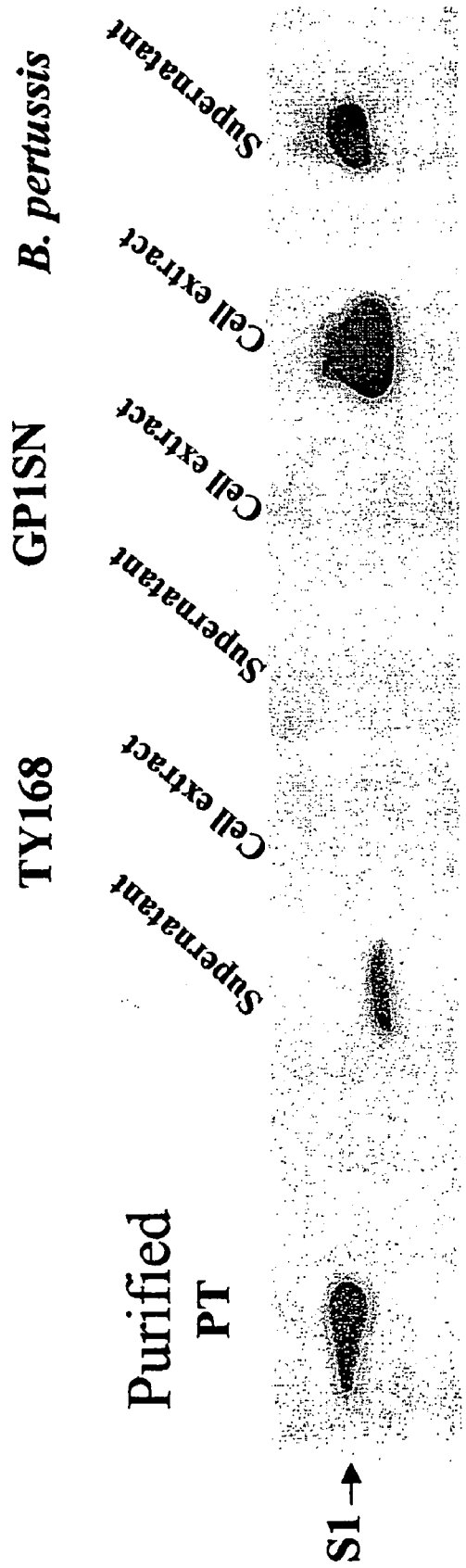
FIG. 3 is an immunoblot analysis of cells and culture supernatant of *Bordetella bronchiseptica* Strain TY168, GP1SN and *Bordetella pertussis* with monoclonal antibody 1B7.

The ability of *Bordetella bronchiseptica* strain TY168 to produce and secrete pertussis toxin was confirmed by immunoblot analysis (FIG. 3). *Bordatella bronchiseptica* strains GPISN and TY168 and *Bordatella pertussis* strain Tohama I were grown to stationary phase and the cells were harvested by centrifugation. The supernatants were concentrated 10-fold by trichloracetic acid precipitation. Cell extracts and supernatants were subjected to SDS-poly acrylamide gel electrophoresis and transferred to nitrocellulose. The blot was probed with monoclonal antibody specific for the pertussis toxin S1 subunit. The results demonstrate that *Bordatella bronchiseptica* strain TY168 is expressing and secreting pertussis toxin.

Figure 4A:
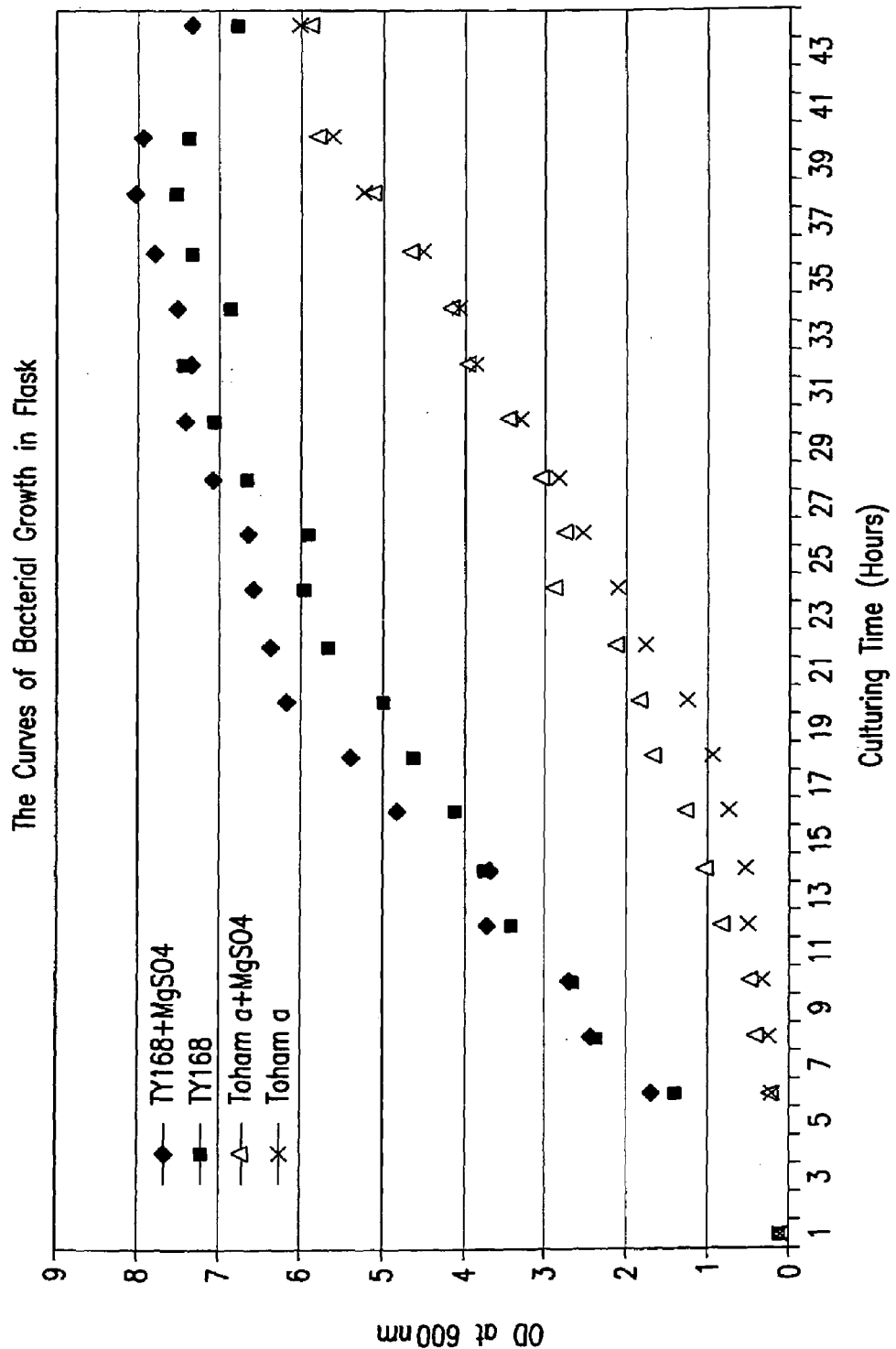
FIG. 4A depicts the growth curve of *Bordetella bronchiseptica* strain TY168.
Figure 4B:
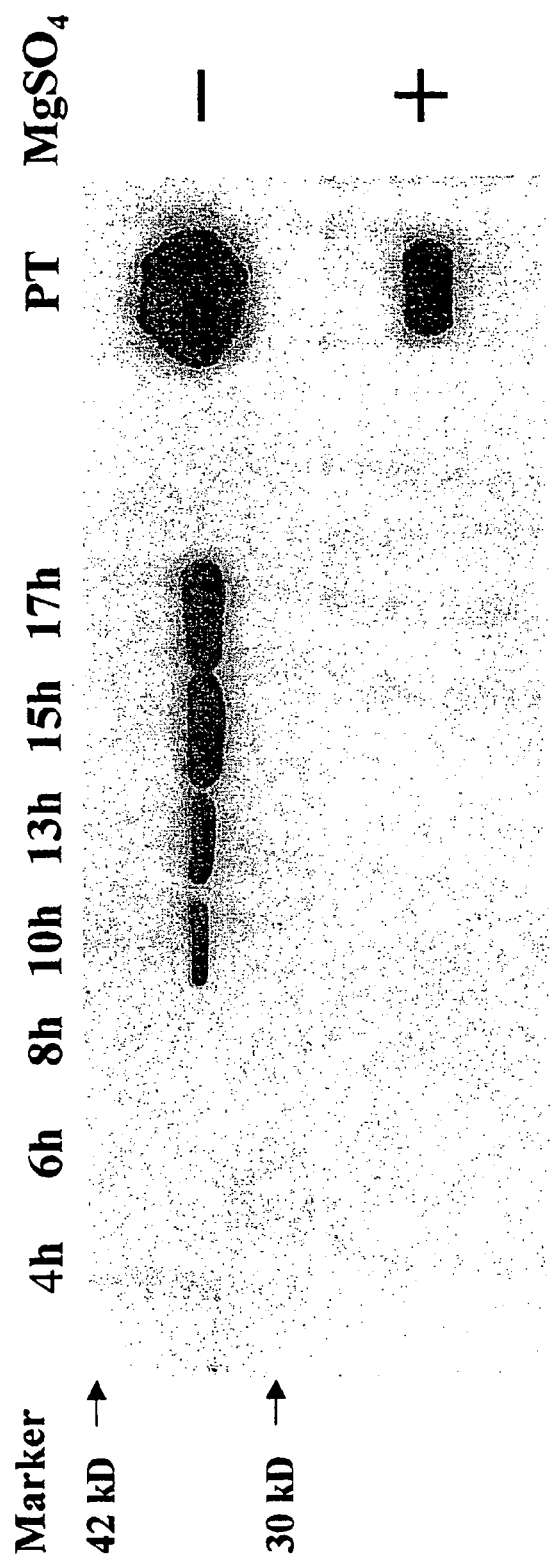
FIG. 4B shows an immunoblot analysis of the culture supernatant of *Bordetella bronchiseptica* strain TY168, expressed as a function of time.

The growth characteristics of strain TY168 were compared to those of pertussis strain Tohama I and the expression of pertussis toxin from strain TY168 was determined as a function of growth (FIG. 4). *Bordatella bronchiseptica* strain TY168 and *Bordatella pertussis* strain Tohama I were grown in liquid culture in the presence or absence of 50 mM MgS04 and the cell density of the cultures was determined every two hours until the cultures reached stationary phase. *Bordatella bronchiseptica* strain TY168 grew at a higher rate and to a higher density than did *Bordatella pertussis* strain Tohama 1. *Bordatella bronchiseptica* strain TY168 was grown in 200 ml liquid cultures in the presence or absence of 50 mM MgSO4. At the indicated time, 5 ml samples were removed from the culture and supernatants were processed and immunoblotted as described in FIG. 3.

Figure 5A:
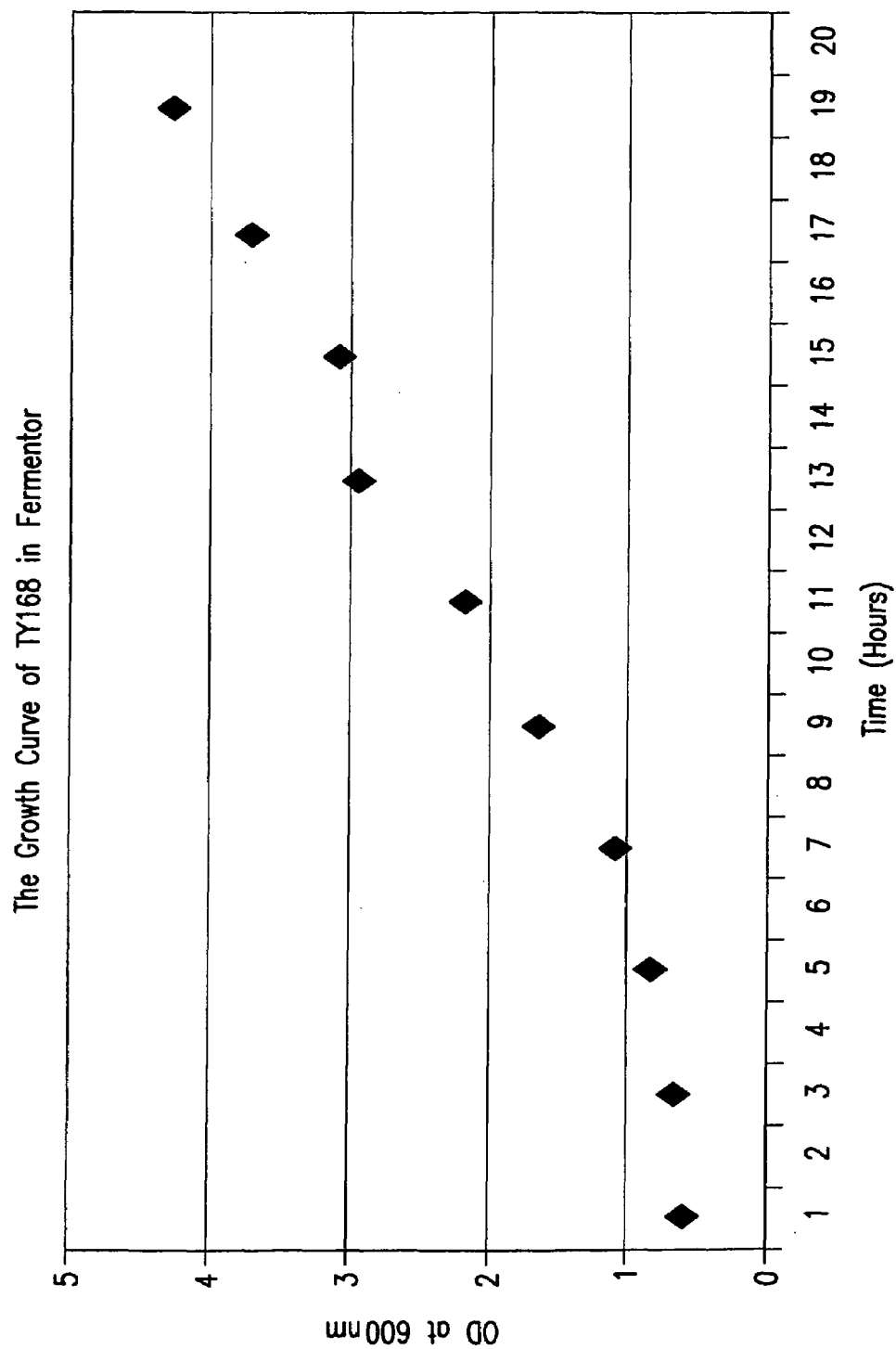
FIG. 5A illustrates the growth curve of strain TY 168 in fermentor.
Figure 5B:
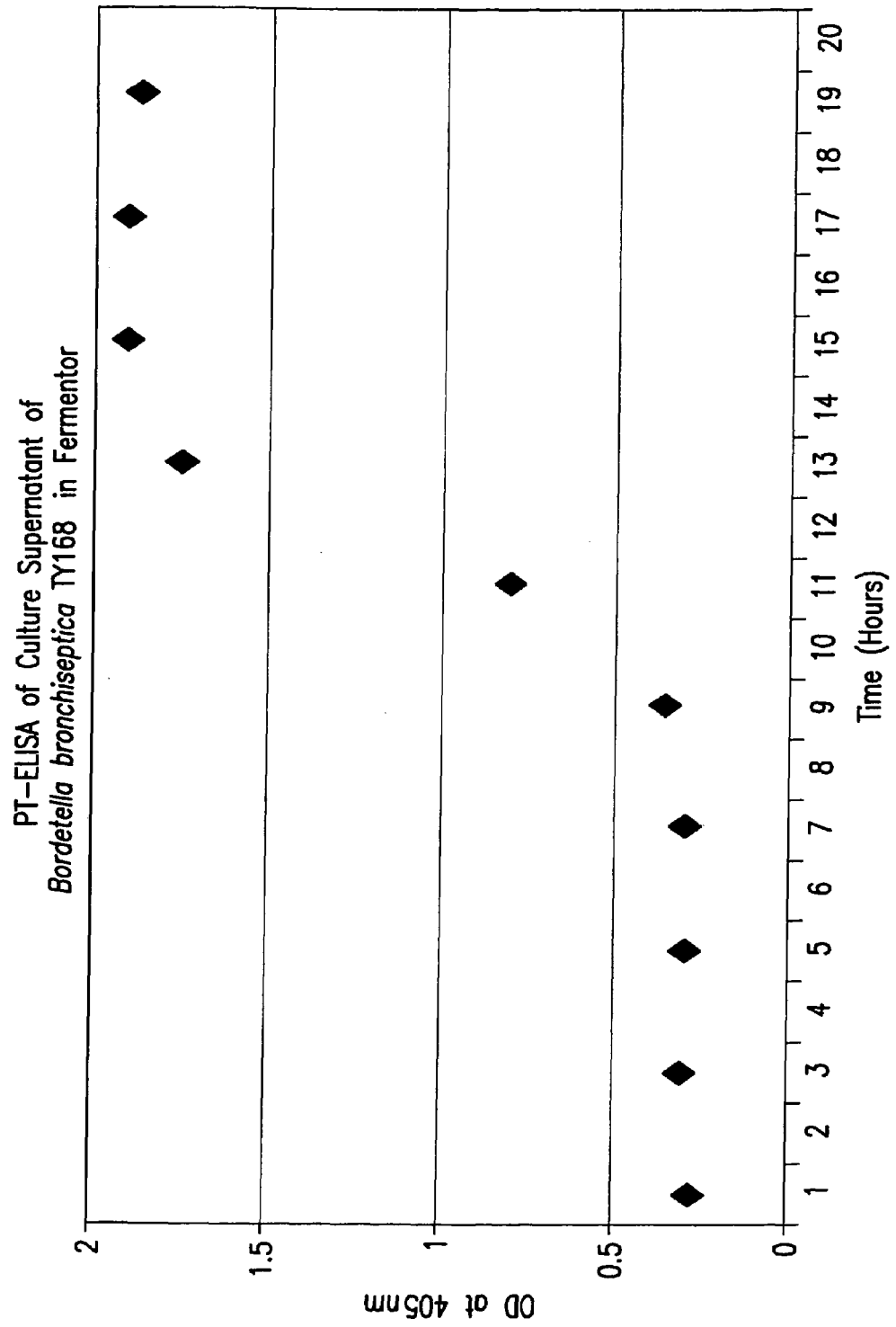
FIG. 5B shows the production rate of pertussis toxin holotoxin.

The results indicate that the expression of secreted pertussis toxin by strain TY168 is regulated normally. Furthermore, it is evident that the toxin accumulates in the supernatant. In order to confirm these results and demonstrate that strain TY168 was secreting assembled holotoxin, a haptoglobin capture ELISA assay was performed (FIG. 5). In this assay pertussis toxin is captured by haptoglobin-coated plates, which specifically bind the *pertussis* toxin B-subunit, and subsequently detected by monoclonal antibody specific for the S1 subunit. Since only toxin with intact B-subunits will be captured and only toxin bearing the A-subunit will be detected, this assay is specific for assembled holotoxin. *Bordatella bronchiseptica* strain TY168 was grown in a six liter fermentor in the presence or absence of 5 mM MgSO4. At the indicated times, 5 ml samples were removed from the culture and supernatants were processed as described above. The results indicate that strain TY168 is producing and secreting assembled holotoxin.

Strain BBPT (TY178) in which the sequences encoding filamentous hemagglutinin were replaced with the gene encoding gentamicin resistance was constructed as follows. First suicide plasmid pTY008 (FIG. 6) was introduced into strain TY168. Isolates in which the plasmid had been incorporated into the bacterial chromosome by homologous recombination between the fhaB regions on the plasmid and the chromosomal fhaB region were identified by selection on colicin-kanamycin plates. In the second step, rare isolates in which the plasmid sequences were crossed out by an intragenic recombination to yield strain BBPT were identified by selecting for loss of the plasmid on plates containing gentamicin and high concentrations of sucrose with subsequent screening for the loss of kanamycin resistance by replica plating of colonies onto plates containing gentamicin and kanamycin.

Figure 7B:
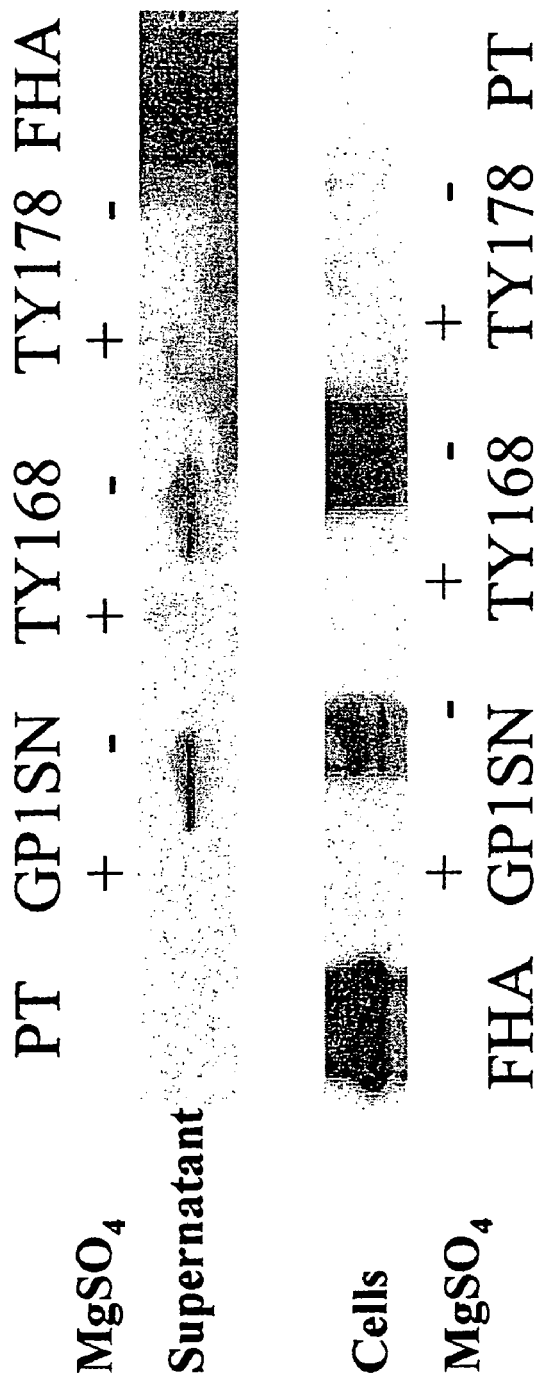
FIG. 7B is an immunoblot analysis of filamentous hemagglutinin with monoclonal antibody MO3.
Figure 8:
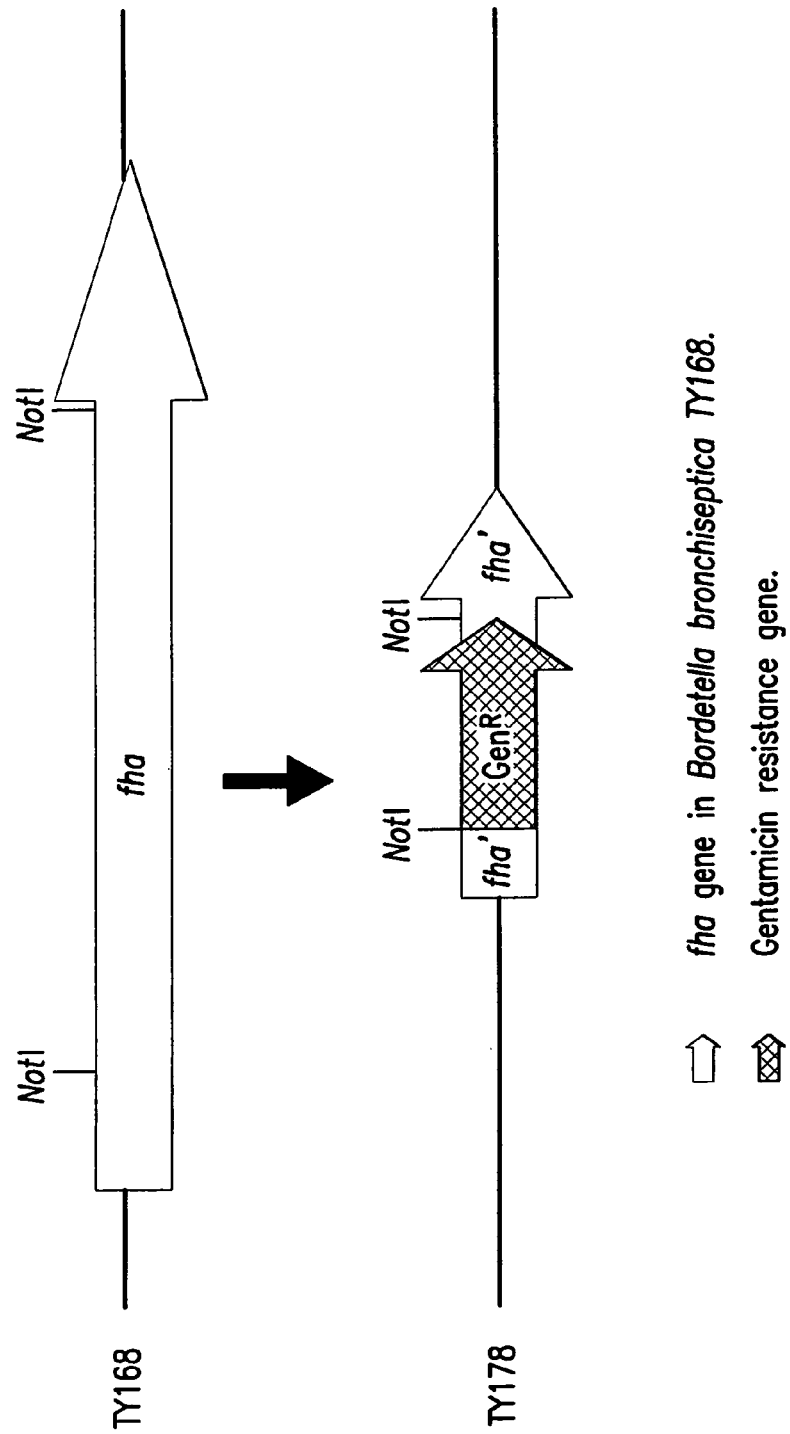
FIG. 8 illustrates the replacement of the filamentous hemagglutinin gene (fha) of strain TY168 with the gentamicin resistant gene ($Gm^R$).

The lack of expression of filamentous hemagglutinin by *Bordetella bronchiseptica* strain BBPT (TY178) and the ability of strain BBPT to produce and secrete pertussis toxin was confirmed by immunoblot analysis (FIGS. 7A and 7B). Strain BBPT and *Bordatella pertussis* strain Tohama I were grown to stationary phase and the cells were harvested by centrifugation. The supernatants were concentrated 10-fold by trichloracetic acid precipitation. Cell extracts and supernatants were subjected to SDS-polyacrylamide electrophoresis and transferred to nitrocellulose. The blot was probed with monoclonal antibody specific for the *pertussis* toxin S1 subunit (FIG. 7A) and monoclonal antibodies specific for filamentous hemagglutinin (fha) (FIG. 7B). The results demonstrate that *Bordatella bronchiseptica* strain TY178 is expressing and secreting pertussis toxin but not fha.

Throughout this application, various publications are referenced. The disclosures of these publications in their entireties are hereby incorporated by reference into this application in order to more fully describe the state of the art to which this invention pertains.

REFERENCES

1. Celplak, W., Burnette, W. N., Mar, V. L., Kaljot, K. T., Morris, C. F., Chen, K. K., Sato, H. and Keith, J. M., Identification of a Region in the S1 Sub-unit of *Pertussis* Toxin that is required for Enzymatic Activity and that Contributes to the Formation of a Neutralizing Antigenic Determinant. *Proceedings of the National Academy of Sciences of the United States of America,* 85:4667–4671 (1988).
2. Burnette, W. N., Celplak, W., Mar, V. L., Kaljot, K. T., Sato, H. and Keith, J. M., *Pertussis* Toxin S1 Mutant with reduced Enzyme Activity and a Conserved Protective Epitope. *Science,* 242:72–74 (1988).
3. Pizza, M., Covacci, A., Bartoloni, A., Perugini, M., Nencioni, L., Demagistris, M. T., Valla, L., Nucci, D., Manetti, R., Bugnoli, M., Giovannoni, F., Olivieri, R., Barbieri, J. T., Satto, H., and Rappuoli, R., Mutants of *Pertussis* Toxin Suitable for Vaccine Development. *Science* 246:497–5000 (1989).
4. Lobet, Y., Feron, C., Dequesne, G., Simoen, E., Hauser, P., and Locht, C., Site-Specific Alterations in the B-Oligomer That Effect Receptor-Binding Activities and Mitogenicity of *Pertussis* Toxin. *Journal of Experimental Medicine* 177:79–87 (1993).

What is claimed is:

1. A bvg-positive *Bordetella bronchiseptica* strain wherein DNA encoding *Bordetella bronchiseptica* toxin is replaced by DNA encoding subunits S1 through S5 of the *Bordetella pertussis* toxin and wherein the *Bordetella bronchiseptica* DNA encoding filamentous hemagglutinin is removed or rendered non-functional, whereby the strain does not express filamentous hemagglutinin.

2. The *Bordetella bronchiseptica* strain of claim 1, wherein the strain is TY178 having the ATCC patent deposit designation PTA-2111.

* * * * *